United States Patent [19]

Owen et al.

[11] Patent Number: 5,065,272
[45] Date of Patent: Nov. 12, 1991

[54] AIR IONIZER

[75] Inventors: Charles W. Owen; Lance Ehren, both of Miami; Frank J. Bianco, Pembroke Pines, all of Fla.

[73] Assignee: Elexis Corporation, Miami, Fla.

[21] Appl. No.: 638,555

[22] Filed: Jan. 9, 1991

[51] Int. Cl.$^5$ ............................................. H01T 23/00
[52] U.S. Cl. ...................................... 361/231; 55/129; 55/141; 55/152
[58] Field of Search ........................ 361/230, 231, 235; 55/129, 141, 150, 152

[56] References Cited

U.S. PATENT DOCUMENTS

| | | | |
|---|---|---|---|
| 1,995,790 | 3/1935 | Anderson | 55/152 |
| 3,624,448 | 11/1971 | Saurenman et al. | 317/4 |
| 3,936,698 | 2/1976 | Meyer | 317/4 |
| 4,264,343 | 4/1981 | Natarajan et al. | 55/126 |
| 4,811,159 | 3/1989 | Foster, Jr. | 361/231 |
| 4,918,568 | 4/1990 | Stone et al. | 361/231 |

Primary Examiner—Brooks H. Hunt
Assistant Examiner—Daniel J. Jenkins
Attorney, Agent, or Firm—Lowe, Price, LeBlance & Becker

[57] ABSTRACT

A portable personal air ionizer includes a dielectric housing small and lightweight enough to be hand carried. The housing contains a circuit for deriving a negative voltage having sufficient value to ionize air molecules, electrodes having pointed ends connected to the high voltage and a ground plane electrode. The negative ions collect airborne particulates which fall by gravity to a collecting pad beneath a stand for fully supporting the housing. Three electrodes are on each of two sheet metal strips, each having an elongated base mounted on a dielectric board. Each electrode is formed as a triangle extending upwardly from the base. The housing includes a central region having an interior wall spaced from an exterior wall. The interior wall forms a well where the circuit is located, surrounded and held in place by a potting compound. An edge of the dielectric board abuts against a dielectric wall between the ground plane electrode and the pointed electrodes. The board is tilted upwardly with respect to the ground plane electrode, with the pointed electrodes extending generally at right angles to the board. The electrodes are dimensioned and positioned relative to each other to clear smoke from an enclosed one cubic foot volume in less than approximately one minute, even though the ionizer does not include a fan.

33 Claims, 3 Drawing Sheets

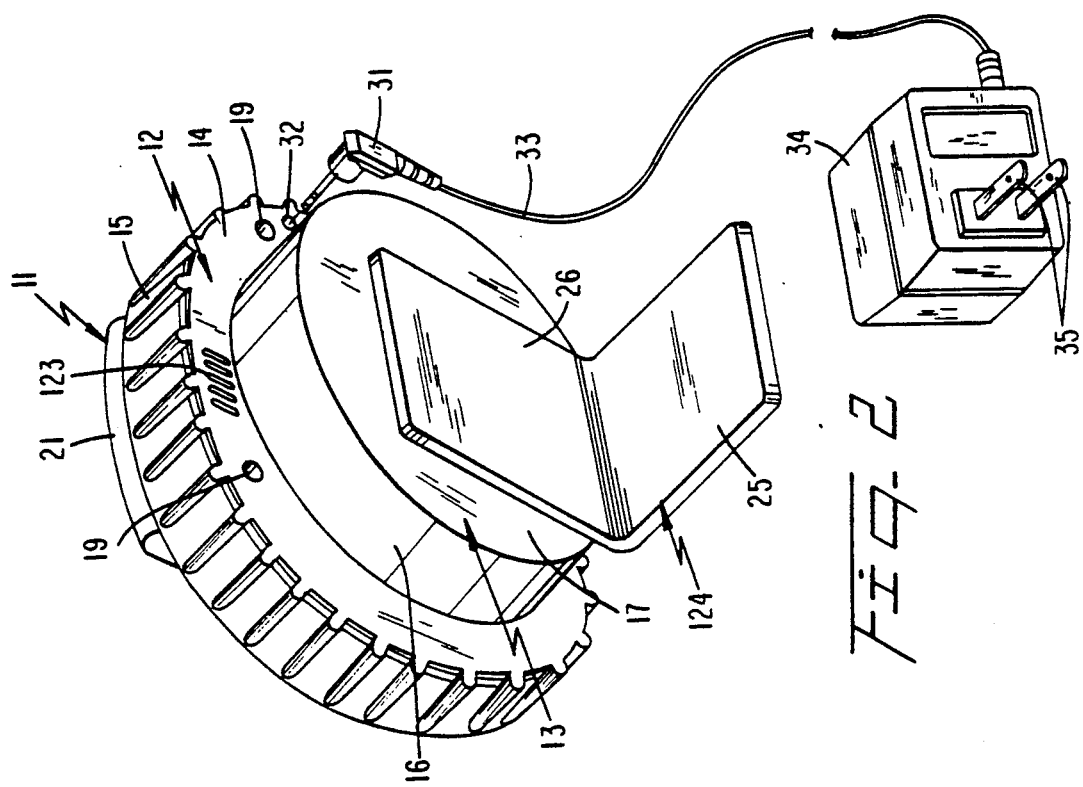
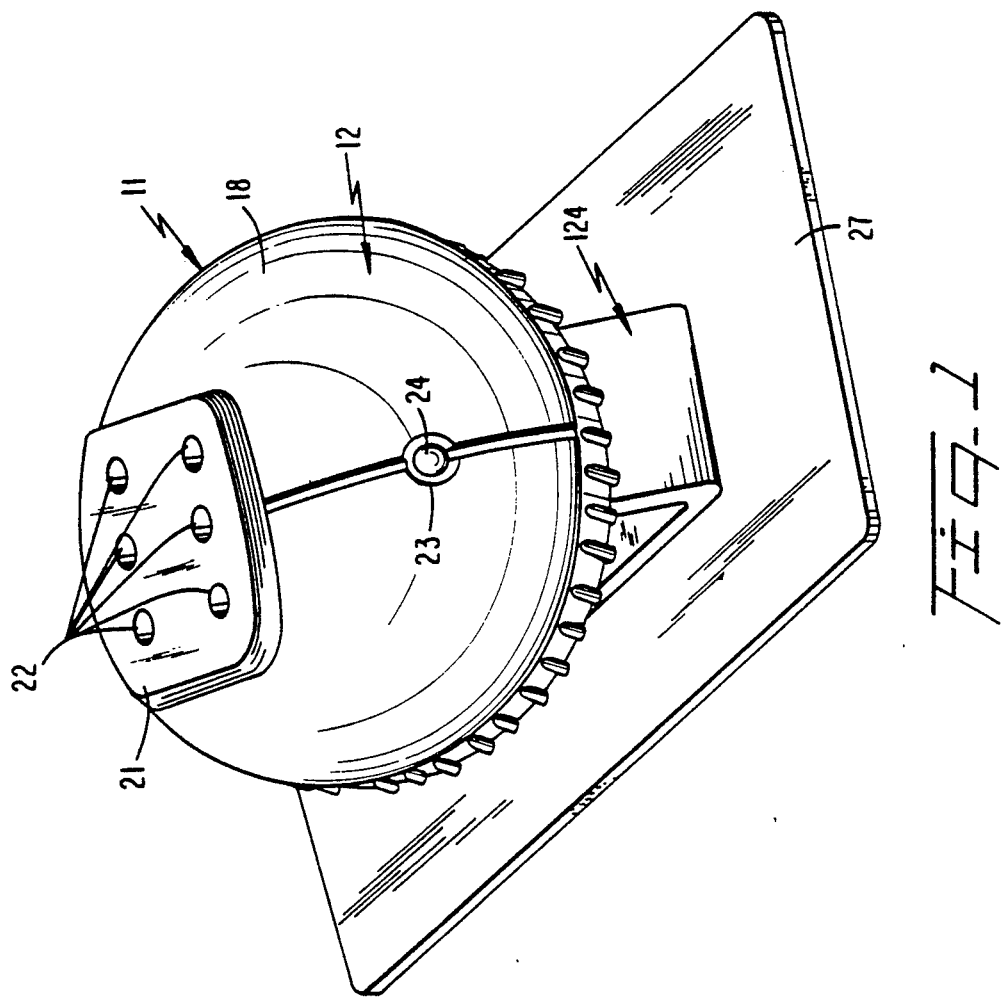

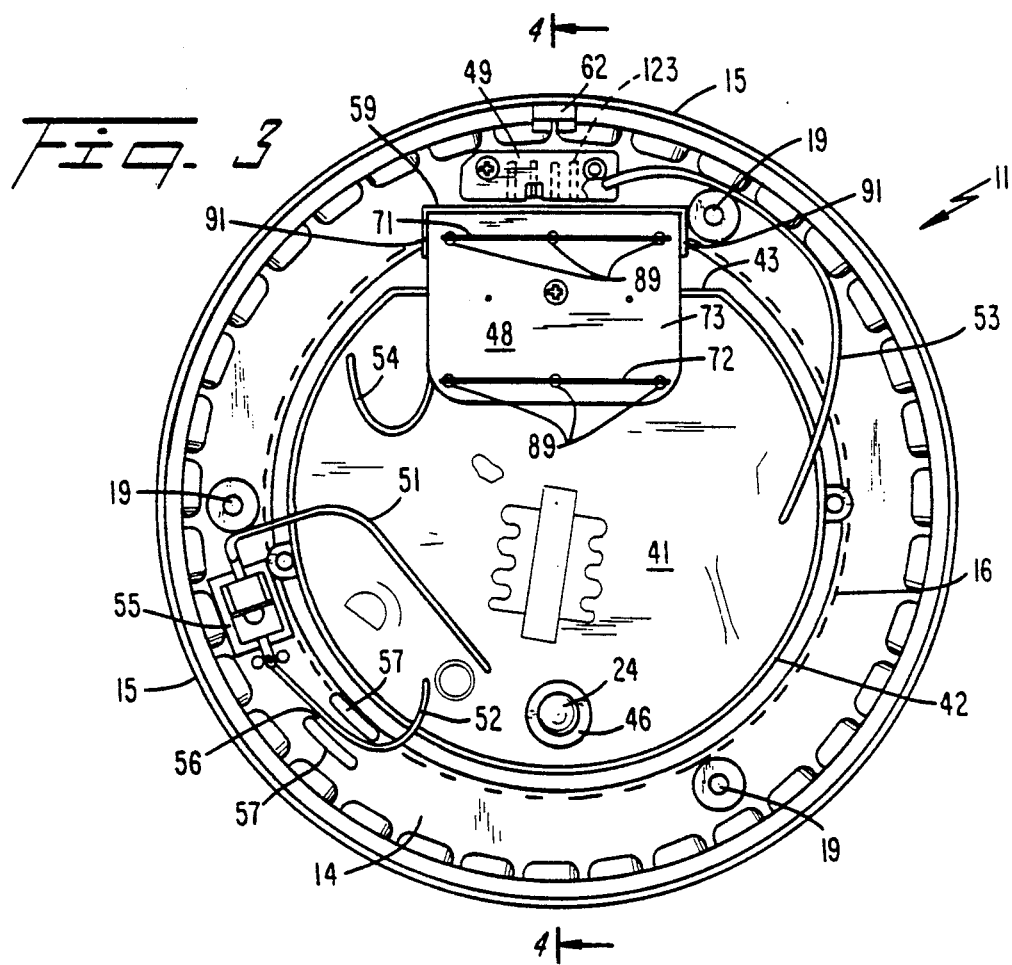
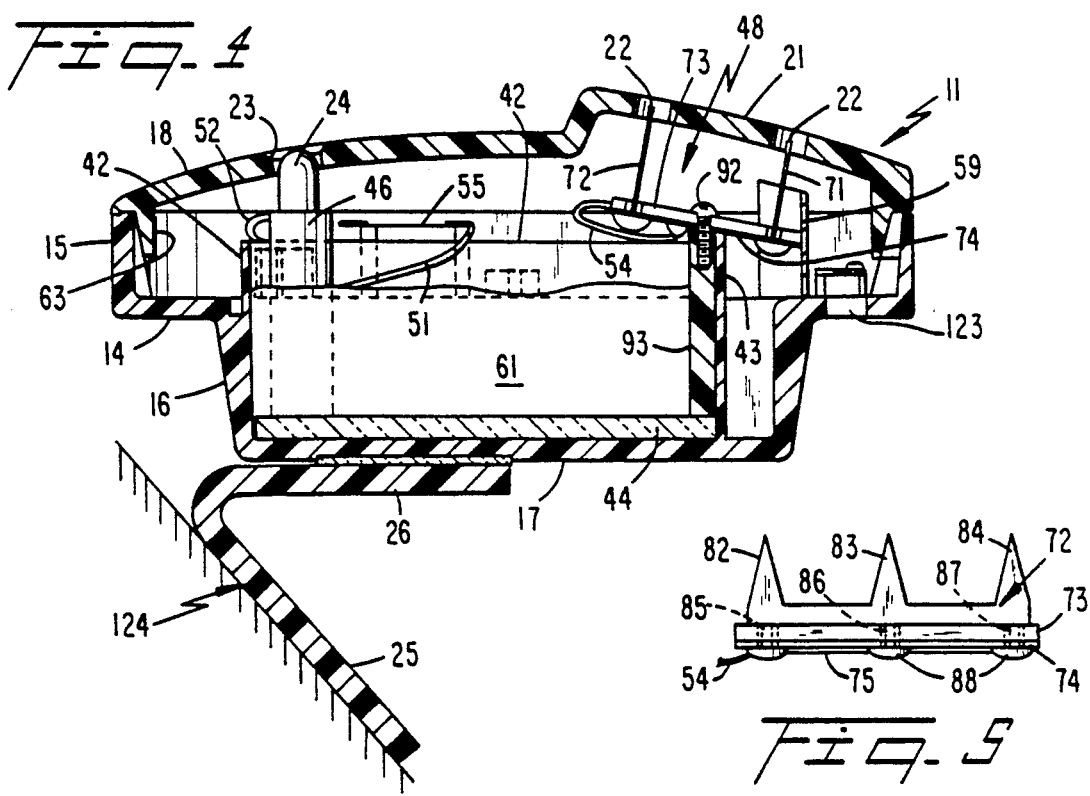

AIR IONIZER

FIELD OF INVENTION

The present invention relates generally to personal air ionizers small and lightweight enough to be held in a hand for removing particulates from air in home, office and light industrial environments, and, more particularly, to such an air ionizer having no fan, but which includes several features enabling it to be relatively inexpensive and effective to remove particulates from home, office or light industrial environments.

BACKGROUND ART

It has long been known that formation of negative ions in the atmosphere reduces particulates, such as smoke, dirt and pollen. Apparently, the particulates are attracted to the negative ions, each of which forms a nucleus. A substantial number of the particulates collect on the nucleus and eventually attain a sufficiently great density to cause the accumulated particles to fall by gravity. Many of the prior art air ionizers employ fans, apparently to assist in drawing the particulates into the region where the negative ions are located. Air ionizers employing fans, however, are relatively large, expensive and somewhat noisy.

It has been realized that particulates can be precipitated and collected without the use of a fan. Such an air ionizer is disclosed in Foster, Jr., U.S. Pat. No. 4,811,159, wherein negative ions are emitted from an array of needle electrodes in a housing. It is reported that a "wind" can be observed with this prior art device. This particular prior art device is adapted to be plugged directly into a wall outlet connected to a 60 Hz, 120 volt electric main. The Foster, Jr. air ionizer is allegedly designed so that the precipitated particulates are collected on a pad, maintained at ground potential, inside of the housing containing the needle electrodes. However, it has been found that the precipitated particulates frequently accumulate on a wall where the outlet is located, rather than on the pad within the housing. Hence, the wall next to the outlet quickly becomes dirty.

It is, accordingly, an object of the present invention to provide a new and improved relatively inexpensive personal air ionizer in a housing small and lightweight enough to be hand-held wherein precipitated particulates resulting from the air being ionized are collected on a pad on which the housing is located.

Another object of the present invention is to provide a new and improved fan-less personal air ionizer small and lightweight enough to be hand-held, and which has an improved electrode array that reduces manufacturing cost.

An additional object of the present invention is to provide a new and improved fan-less personal air ionizer small and lightweight enough to be hand-held, and which has an improved mechanical arrangement for inexpensively fixedly locating high voltage power supply components and providing them with good breakdown characteristics.

A further object of the invention is to provide a new and improved relatively inexpensive personal air ionizer located in a fan-less housing small and lightweight enough to be hand-held, wherein electrodes in the housing are arranged so that a volume of one cubic foot of smoke is cleared in less than one minute.

THE INVENTION

In the present invention, a portable air ionizer comprises a dielectric housing small and lightweight enough to be hand-held and including: a circuit having high voltage and ground output terminals for converting an input voltage into a negative high voltage, a ground plane electrode and an array of plural electrodes having pointed ends. The negative high voltage has sufficient value to ionize air molecules. The circuit high voltage and ground terminals are respectively connected to the plural electrodes having pointed ends and the ground plane electrode. The housing further includes an opening in proximity to each of the electrodes, such that the openings proximate the electrodes having pointed ends are on an upper surface of the housing and the opening proximate the ground plane electrode is on a lower surface of the housing. The openings and electrodes are positioned and arranged and the voltage applied to the plural electrodes are such that negative ions flow from the plural electrodes through the apertures proximate thereto to produce a "wind" above the apertures, even though no fan is in or associated with the housing. The negative ions cause particulates to be collected in the air above the upper surface. The collected particulates thereby fall by gravity.

In accordance with one particular feature of the invention, the housing is positioned on a stand, in turn placed on a collection pad for the particulates; the pad is adapted to be placed on a horizontal surface. The collected particulates fall by gravity unto the pad. Such a pad is easily cleaned with a suitable liquid solvent, e.g. a water-detergent mixture. This structure avoids the problems of dirt collecting on a wall adjacent the housing, as in the above described prior art air ionizer. In additional, the housing is preferably arranged on the stand so no portion of the housing contacts the pad and the housing is fully supported by the stand. In actual experiments wherein the dielectric housing contacted the dielectric pad, the particulates had a tendency to accumulate over a region having a radius of about one foot from the intersection of the pad and the housing. By fully supporting the housing on the stand so the lowest portion of the housing is spaced by about 9/16 inch from a dielectric collection surface, the collection region is reduced to a radius of about two inches, enabling a relatively small 5×7 inch rectangular collection pad to be used. No difference in the time required to remove smoke from an enclosure occurred even though the collection area decreased.

In accordance with a further feature of the invention, the plural electrodes are included on a sheet metal strip having an elongated base from which extend plural triangles, each having an apex remote from the elongated base to provide a formation location for the negative ions. The strip is connected to the high voltage terminal. A pair of such strips is mounted on a dielectric board including printed circuit wiring connecting the sheet metal strips to the high voltage terminal. The strips are flat and extend along lines on the printed circuit board that are substantially parallel to each other, such that the apices of the different strips are aligned with each other. In addition, each strip includes at least one post that extends from the base in a direction opposite from the apices of the triangles. The posts are embedded in the printed circuit board and connected by the printed circuit wiring to the high voltage terminal. Such an arrangement is particularly advantageous because the electrodes are easy to manufacture, keep track of during inventory and handing, and are easily held in place and inserted onto the printed circuit board. There is, thereby, a substantial reduction in cost, relative to the cost of dealing with individual electrodes that are basically formed as needles.

According to a further feature of the invention, the housing includes a central region having an interior wall spaced from an exterior wall of the housing. The interior wall forms a well in which the circuit is located. The circuit is surrounded and held in place in the well by a potting compound that fills the well and becomes bonded to the interior wall. This construction enables a printed circuit board carrying the converter circuit to be easily dropped in place into the well. The well includes one straight wall conforming in size to an edge of the printed circuit board so that the printed circuit board invariably is placed in the correct position in the well. The potting compound and the interior walls cooperate to effectively stabilize the position of the circuit, with a minimum of expense. The potting compound has a relatively high dielectric strength to thereby help to prevent possible voltage breakdowns between low and high voltage components on the circuit, as well as between high voltage components of the circuit and the ground plane.

The ground plane and a connector between a source of the input voltage and the converting circuit are located in the housing between the solid dielectric interior and exterior walls, to facilitate placement of these components and thereby reduce cost In addition, the low voltage components connected to the input source and the ground plane are spaced from the high voltage components by the relatively high dielectric strength wall.

In accordance with a further feature of the invention, the plural electrode array is mounted on a dielectric board and a dielectric wall is positioned between the ground plane electrode and the electrode array. The dielectric board is mounted so that an edge thereof abuts against the dielectric wall, to provide ease of construction, as well as to provide breakdown protection between the high voltage applied between the pointed electrodes on the dielectric board and the ground plane.

As a further feature of the invention, the pointed electrode array and the ground plane electrode are positioned relative to each other so that a confined one cubic foot volume of smoke laden air is cleared in less than one minute in response to a negative voltage of approximately 3,000 volts being applied to the electrode array relative to the ground plane electrode. It has been found through experimentation that the relative positioning of the electrode array and the ground plane provides this result, such that there is visual swirling of the smoke particles in the confined volume. The electrode array is arranged so that there are two parallel rows of pointed electrodes. Each row includes three pointed electrodes having a total height of approximately ⅜ inch above a dielectric board on which the electrodes are mounted. There is a space of approximately ½ inch between the points of adjacent electrodes along each row, with a row spacing of approximately ¾ inch. The electrodes are tilted so that they are approximately 60° above the horizontal on which the collecting pads is located. There is about ½ inch vertical space between the tips of the electrodes (i.e., the apices of the triangles forming the electrodes) and the ground plane. The horizontal distance between the apices and an edge of the ground plane is approximately 1/16 inch.

It was found, through actual experimentation, that this particular position provided optimum particulate precipitation. As the ground plane was moved to differing locations in the housing, to be more remote from the electrode array, smoke stratification occurred in the one cubic foot enclosed volume. The smoke stratification resulted in a considerably longer time requirement to remove the smoke from the enclosed one cubic foot chamber than for the actually employed configuration.

In the experiments, a bundle of twelve burning fragrance sticks was inserted into a cubic transparent enclosure having edges one foot long for a period of two minutes prior to the ionizer being supplied with power, at which time the sticks were removed. When power was applied to the ionizer, the enclosure appeared to be completely opaque to the eye due to the smoke therein. In the preferred embodiment, the smoke swirled for about one to two inches above each pointed electrode. The six swirling funnel-like patterns combined into a single swirling pattern about four inches above the pointed electrodes. After about 45 seconds of ionizer operation, it was possible to see between opposite sides of the cube; based on visual observations after one minute, the air in the enclosure was smoke-free.

This test was repeated several times with basically the same results for the stated position of the electrodes. However, when the same test was tried with different positions of the electrodes, smoke stratification occurred and the time to achieve the results attained in one minute with the preferred embodiment was increased several times. The only known currently available prior art commercial personal ionizers that do not use a fan were tested under the same conditions. Neither the POLLENEX ionizer of U.S. Pat. No. 4,811,159 nor the other commercial personal ionizer without a fan produced any visual swirling smoke patterns. Instead, when both of these ionizers were tested, smoke stratification occurred in the volume above the electrodes and was visually observed even more than five minutes after power was supplied to the units. Hence, the preferred embodiment of the present invention provides considerably improved results not attained by the prior art of which we have knowledge nor by other electrode positions in the housing arrangement of the present invention.

A further feature of the invention is that the input voltage is provided by a conventional jack. The jack is connected to a cable, in turn connected to a standard step down voltage device, which may convert AC current from a 60 Hz, 120 volt AC main to a low voltage DC, or reduce the voltage from a 12 volt source, e.g. an automobile battery, to a suitable level. Hence, the air ionizer may be used in many different environments. For example, the housing could be mounted in an automobile, with excitation voltage being provided by a cigarette lighter plug or on a desk or table in an office, factory or home, with excitation from a wall outlet.

The above and still further objects, features and advantages of the present invention will become apparent upon consideration of the following detailed description of a specific embodiment thereof, especially when taken in conjunction with the accompanying drawings.

BRIEF DESCRIPTION OF DRAWING

FIG. 1 is a generally front perspective view of a preferred embodiment of an air ionizer of the invention;

FIG. 2 is a generally rear perspective view of the ionizer illustrated in FIG. 1;

FIG. 3 is a front view of the ionizer illustrated in FIG. 1, with the front cover removed;

FIG. 4 is a side view of the ionizer illustrated in FIG. 3, taken through the lines 4—4;

FIG. 5 is a front view of an electrode assembly mounted on a printed circuit board included in the ionizer illustrated in FIGS. 3 and 4.

DESCRIPTION OF THE PREFERRED EMBODIMENT

Figure 6:
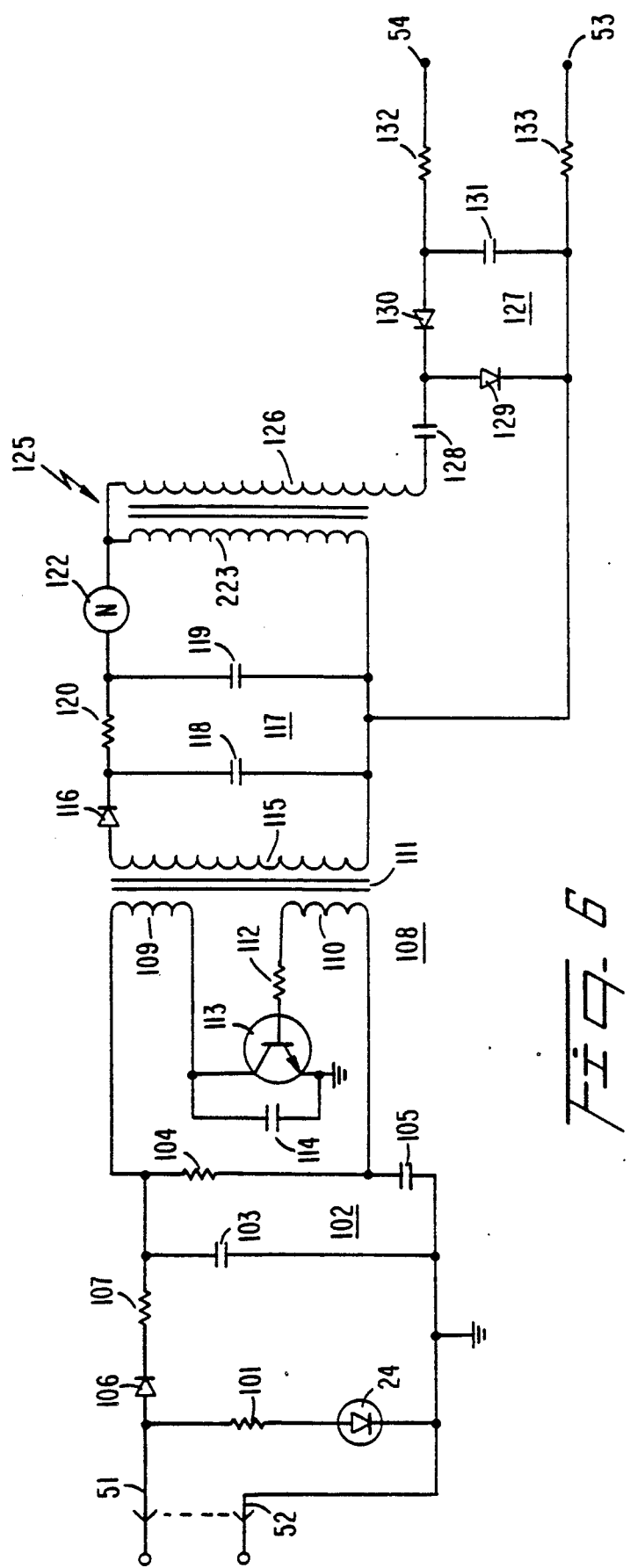
FIG. 6 is a circuit diagram of a preferred embodiment of a high voltage supply included in the ionizer illustrated in FIGS. 1-4.

Reference is now made to FIGS. 1 and 2 of the drawing wherein hard molded plastic, dielectric, housing 11 is illustrated as including disk-like upper portion 12, carried by disk-like lower portion 13. Disks 12 and 13 respectively have radii of 4 inches and 2¾ inches, with heights of approximately ½ inch and ⅜ inch, respectively. The weight of housing 11 and contents is approximately ¼ pound, so that the housing and its contents can be easily held in the hand of a human and the housing can be placed unobtrusively on a desk, counter, etc. in a home, office, or light industrial environment. Ledge or flange 14 extends between and is connected to coaxial circular walls 15 and 16 of disks 12 an 13. The bottom or back of housing 11 is formed by circular plate 17, while the top or front of the housing is formed by removable circular cover 18, selectively secured in situ by screws (not shown) extending through three recessed bores 19 (only two of which are shown) into threaded bores and sleeves (not shown) that extend downwardly from cover 18.

Cover 18 is slightly convex and includes ridge 21 on its upper portion, as mounted in situ on disk 12. Extending through ridge 21 are six bores 22, arranged in two parallel rows. Bores 22 in the two parallel rows are aligned so that the center bores in each row extend along a radius of circular cover 18, with the bores on either side of the center bores being equispaced from the center bores. In each of bores 22 is an elongated electrode having a sharp end, defined by an apex of a triangle, slightly below the surface of ridge 21. The electrodes form an array supplied with a negative voltage causing negative ions to be formed in the air above bores 22; the negative ions in the atmosphere above bores 22 form a "wind" in the air.

Cover 18 also includes bore 23, through which LED 24 extends. LED 24, when activated, indicates that the ionizer is energized.

In use, dielectric support bracket 124 is fixedly attached to back plate 17. Bracket 124 includes horizontal leg 25 (that rests on a horizontal surface) and leg 26 that is inclined upwardly at 45° relative to the horizontal leg. Plate 17 is attached to the upper face of leg 26 by any suitable means, such as a double-backed adhesive pad. Because leg 26 is disposed 45° at leg 25, plate 17 and ledge 14 are disposed at an angle of 45° relative to the horizontal.

On ledge 14, immediately behind ridge 21, are five elongated slots 123 that extend in a direction generally parallel to the direction between the two rows of bores 22. Immediately behind slots 123 is a ground plane electrode, maintained at ground voltage.

Apparently, the negative ions formed in the air above bores 22 are attracted to particulates in the atmosphere above the bores. The negative ions apparently cause formation of nuclei for the particulates in the atmosphere. After the particulates have accumulated to a sufficient degree, they fall by gravity toward the ground plane electrode, and pass the ground plane electrode to the surface on which leg 25 of support bracket 124 is located. To prevent the desk, counter or other object which supports bracket 124 from becoming excessively dirty, leg 25 rests on polyethylene collector mat 27, having a rectangular 5×7 inch area in the preferred embodiment. Thereby, the particulates which are precipitated from the atmosphere as a result of the interaction between the particulates and the negative ions fall to and are collected by mat 27. After collector mat 27 has collected a substantial quantity of precipitated particulates, the mat is easily cleaned by use of soap and water, or some other appropriate solvent.

Circuitry within housing 11 is supplied with an energizing voltage by jack 31 that fits into a jack connector in housing 11, immediately behind ledge 14. The connector in housing 11 is connected to jack 31 by a metal sleeve (not shown) in bore 32 that extends through ledge 14. The sleeve holds the connector in place and provides an electrical connection from a grounded wire of cable 33 to a grounded terminal for the connector. Jack 31 is connected by cable 33 to AC to low voltage DC converter 34. Converter 34 is of the conventional type including male outlet plugs 35 that fit into a wall socket connected to a 60 Hz, 120 volt AC main. AC to DC converter 34 supplies cable 33 and jack 31 with a low voltage output, such as 9 or 12 volts, that is converted by circuitry in housing 11 to high negative voltage that is applied to the electrodes in bores 22. The connector in housing 11 that receives jack 31 can receive jacks from other DC sources, such as DC to DC converters that are energized by automobile cigarette lighter sockets.

Reference is now made to FIG. 3 of the drawing, a top view of housing 11 with cover 18 removed. The interior of housing 11 includes well 41 formed by arcuate wall 42 and straight wall 43 which project upwardly from ledge 14, slightly inside of wall 16 of hollow disk 13. Wall 42 is formed as a segment of a circle having a center coincident with the common center of circular walls 15 and 16. Wall 43 connects the ends of wall 42 together. Dielectric printed circuit board 44, having a peripheral shape that is the same shape as the interior of well 41, as defined by walls 42 and 43, is dropped into the well during assembly. Printed circuit board 44 carries the circuit for converting the voltage supplied to jack 31 into the high voltage for energizing the electrodes of array 48 extending partially into bores 22. Printed circuit board 44 also carries light emitting diode 24 and sleeve 46, both of which extend at right angles from the printed circuit board, as well as post 93 that supports printed circuit board 73 for carrying the high voltage electrodes.

Insulated electric leads 51-54 also extend from and are connected to printed circuit board 44. Lead 51 is also connected to a plate (not shown) in connector 55; the plate is in turn connected to the center electrode (not shown) of jack 31 when the jack is inserted into aperture 32. Lead 52 is at ground potential by a connection to a sleeve of connector 55 that engages the grounded metal sheath of jack 31. Lead 52 passes through channel 56 formed by walls 57 on the interior face of ledge 14, to stabilize the lead position. Leads 51 and 52 supply the DC voltage of jack 31 to components on printed circuit board 44, causing the negative high voltage derived by the converter on the printed circuit board to be derived. The negative high voltage is applied by lead 54 to electrode assembly 48, while lead 53 supplies ground voltage from the circuit on printed circuit board 44 to ground plane electrode 49, secured in place on the interior face of ledge 14 immediately behind slots 23.

Electrode assembly 48 is physically quite close to ground plane electrode 49. Ground plane electrode 49 is separated from the electrodes of assembly 48 by solid dielectric wall 59, to assist in assuring that there is no breakdown between the voltage applied to the electrodes of assembly 48 and ground plane electrode 49.

After printed circuit board 44 has been dropped into well 41 with the aforementioned connections having been made to leads 51-54, the well is filled with epoxy dielectric potting compound 61 (FIG. 4). Epoxy potting compound 61 fills well 41 and surrounds sleeve 46 as well as post 93 for supporting the printed circuit board on which electrode assembly 48 is mounted. Epoxy potting compound 61 abuts against and is bonded with the interior surfaces of walls 42 and 43, to hold printed circuit board 44 and the components thereon in situ in well 41, while providing a high breakdown strength material to assist in preventing voltage breakdown between the components on printed circuit board 44, as well as between other components in housing 11. This arrangement enables manufacturing costs to be minimized, while providing the necessary high voltage protection, as well as mechanical stability for printed circuit board 44 and the components thereon, as well as for leads 51-54 as they extend from compound 43.

To secure cover 18 on wall 15 and to facilitate placement of the cover on the wall, wall 15 includes indented guide 62, formed as a square to receive a square base on rim 63 that extends downwardly from the remainder of cover 18, having a peripheral rim (not shown) that engages a peripheral lip (not shown) on the upper portion of wall 15. Bolts (not shown) inserted through bores 19 are screwed into threaded bores (not shown) in sleeves extending downwardly from the interior face of cover 18 so that the cover is securely attached to the lower portion of housing 11 including disks 12 and 13.

Light emitting diode (LED) 24 extends from sleeve 46 which is positioned on printed circuit board 44 so that the LED extends into aperture 23 on cover 18, to a point slightly below the top face of the cover.

Electrode assembly 48 is formed as two identical stamped sheet metal, stainless steel strips 71 and 72, each including three triangles (similar to needles) that extend into bores 42 on ridge 21. Strips 71 and 72 extend parallel to each other and to wall 59, as well as to the longitudinal axis of ground plane electrode 49, having a rectangular shape. The apices of the triangles are slightly below the top, i.e. exterior, surface of ridge 21 so that it is relatively difficult for a person to touch the apices of the triangles, while enabling the apices to be sufficiently close to the top of the ridge to cause formation of negative ions in the bores; the negative ions are ejected into the atmosphere. Stainless steel strips 71 and 72 are positioned parallel to each other and are carried by ceramic board 73 having a high breakdown strength to prevent possible voltage breakdown between the electrodes of array 48 and ground plane electrode 49. Ceramic board 73 is secured to dielectric printed circuit board 74 having metallized printed circuit leads 75 on the lower surface thereof, i.e., the surface remote from the surface of the printed circuit board that abuts against ceramic board 73. The metallized printed circuit leads 75 on printed circuit board 74 are connected to lead 54.

As illustrated in FIG. 5, stamped stainless steel sheet metal electrode strip 72 includes an elongated base 73 that extends horizontally along and in abutting relationship with the top surface of ceramic board 73. Extending upwardly from strip 81 are identically shaped isosceles triangles 82, 83 and 84, which form the needle electrodes that fit into bores 22. The apices of triangles 82-84 are in a straight line, at the same distance above the top of strip 81 and below the top surface of ridge 21. The apices of triangles 82-84 are equispaced from each other.

Extending downwardly from strip 81 are posts 85-87, respectively aligned with triangles 82-84. Posts 85-87 extend through aligned bores in boards 73 and 74 and are secured to the boards by solder joints 88 to printed circuit leads 75.

Electrode strip 71 is constructed identically to electrode strip 72. The corresponding apices of triangles 82-84 of strips 71 and 72 are aligned, as indicated by dots 89, FIG. 3.

Boards 73 and 74 are installed so that the edges of the boards adjacent and parallel to strip 71 abut against the face of wall 59 closest to wall 43 of well 41. Extending at right angles from opposite edges of wall 59 are flanges 91 against which the edges of boards 73 and 74 approximately abut, to assist in positioning the boards in housing 11. Boards 73 and 74 are secured in place by bolt 92 that is threaded into a threaded bore of post 93 that projects upwardly from printed circuit board 44, just on the inner face of wall 59. The upper face of post 93, on which the bottom face of board 74 rests, is tilted backwardly at an angle of approximately 15° so that boards 73 and 74 are likewise tilted with respect to the planes of plate 17 and ground plane electrode 49. Since strips 71 and 72 extend at right angles from the face of ceramic board 73, triangular electrodes 82-84 of strips 71 and 72 are tilted away from the common center line of walls 15 and 16 by an angle of 15°. In consequence, with housing 11 mounted on support bracket 124 and the support bracket being positioned on pad 27, as illustrated in FIG. 1, the planes defined by the faces of strips 71 and 72 are inclined at an angle of 60° relative to horizontally extending pad 27.

In the preferred embodiment, each of electrode strips 71 and 72 has a length of approximately 1¼ inches and a height, from the bottom edge of the strip in contact with ceramic board 73 to the top of the apices of triangles 82-84, of approximately ⅜ inch. Each of triangles 82-84 has a height of approximately ¼ inch and a base of approximately ¼ inch. The apices of adjacent pairs of triangles on one of strips 71 and 72 are spaced from each other by approximately ½ inch, i.e., the apices of triangles 82 and 83 of strip 72 are spaced from each other by approximately ½ inch. Strips 71 and 72 are spaced from each other by approximately ¾ inch.

Stamped sheet metal ground plane conductor 49 has a length of approximately ¾ inch and a width of approximately ¼ inch. Electrode strips 71 and 72 and ground plane electrode 49 are positioned so that the vertical distance between the ground plane electrode and the apices of triangles 82-84 is approximately ½ inch, while the horizontal distance between the edge of the ground plane closest to wall 59 to the apices of triangles 82-84 of strip 71 is about 1/16 inch. (In the foregoing sentence, the terms vertical and horizontal refer to directions at right angles to ground plane 49 and in the direction of the ground plane.)

It has been found through actual experimentation that the aforementioned geometry and dimensions enable the ionizer of the present invention, when energized by the circuit illustrated in FIG. 6, to clear smoke from a one cubic foot enclosed volume in less than one minute. This is considerably better than for other relative positions for the ground plane and needle electrodes that were experimentally tried. With the described preferred arrangement, it is possible to visually observe swirling of the smoke as a result of the "wind" resulting from the negative ions. In other configurations of the electrodes which were tried, it was noted that stratification of smoke in the enclosed one cubic foot volume occurred. The stratification of smoke was not accompanied by visual swirling. Stratification caused a significant increase in the time required to remove smoke from the volume.

Reference is now made to FIG. 6 of the drawing, a circuit diagram for converting the DC voltage applied to leads 51 and 52 into the ground and high voltages applied by leads 53 and 54 to ground electrode 49 and to electrode strips 71 and 72, electrically connected in parallel with each other to be responsive to the voltage applied to lead 54. The voltage applied to leads 51 and 52 is applied to LED 24 by current limiting resistor 101, connected in series with the LED; the series combination of resistor 101 and LED 24 is in shunt with leads 51 and 52. The voltage between leads 51 and 52 is smoothed further by a low pass filter circuit 102 including shunt capacitor 103, connected in parallel with the series combination of resistor 104 and capacitor 105. Low pass filter 102 is connected to be responsive to the DC voltage on lead 51 by diode 106 and current limiting resistor 107.

The DC voltage developed across resistor 104 energizes oscillator 108, including windings 109 and 110 of transformer 111. One end of winding 110 is connected by current limiting resistor 112 to the base of grounded emitter bipolar NPN transistor 113, having a collector connected to one terminal of winding 109. The emitter collector path of transistor 113 is shunted by capacitor 114 to prevent excessive back voltage across the transistor emitter collector path.

Transformer 111 includes output winding 115, across which is developed a 200 Hz wave having a several hundred volt peak to peak value. The voltage developed across winding 115 is converted into a DC voltage by rectifier 116 and low pass filter 117 including shunt smoothing capacitors 118 and 119, as well as series resistor 120. The voltage developed across capacitor 119 is applied to SIDAC 122, connected in series between a common terminal for capacitor 119 and resistor 120 and one terminal of primary winding 223 of transformer 124. SIDAC 122 is a voltage triggered switch which becomes conducting in response to the voltage across it exceeding a predetermined threshold level.

Transformer 125 includes secondary winding 126 across which is developed an AC voltage having a peak to peak value in excess of 1,000 volts. The voltage developed across transformer 126 is applied to voltage doubler 127 including series capacitor 128, shunt diode 129, series diode 130 and shunt capacitor 131. Resistor 132 is connected between the common terminal of diode 130 and capacitor 131 and lead 54. Circuit 127 is a relatively conventional voltage doubler, except that capacitors 128 and 131 have differing values; in the preferred embodiment, capacitors 128 and 131 respectively have values of 95 picofarads and 50 picofarads, which were found experimentally to provide the fastest rate for smoke removal from the enclosed one cubic foot volume. The common electrodes of diode 129 and capacitor 131 are connected to common electrodes of capacitors 118 and 119 and to one terminal of resistor 133, the other terminal of which is connected to lead 53.

In tests actually conducted with a TEKTRONIX oscilloscope model 464 and a 100:1 voltage divider probe it was found that negative voltage pulses are developed at lead 54 relative to the voltage of lead 53 and ground plane electrode 49. The negative pulses have a zero DC base line, a peak-to-peak value of about 3 kilovolts and a frequency of approximately 125 Hz. Oscilloscope traces taken with a 100:1 voltage divider probe connected to leads 53 and 54 indicate that the leading negative going edge of each pulse, that apparently occurs in synchronism with each firing of SIDAC 122, has a very steep slope. After the leading edge, there is an exponential increase in the voltage to about a zero volt level. Shortly after or simultaneously with the zero volt level being reached, the steep negative going transition is again derived. It was found that the circuit of FIG. 6, when used in conjunction with the apparatus illustrated in FIGS. 1-5, removed smoke particulates from an enclosed one cubic foot volume in somewhat less than one minute and that swirling action of the smoke occurs in the volume, without stratification.

While there has been described and illustrated one specific embodiment of the invention, it will be clear that variations in the details of the embodiment specifically illustrated and described may be made without departing from the true spirit and scope of the invention as defined in the appended claims.

We claim:

1. A portable personal air ionizer comprising a dielectric housing small and lightweight enough to be hand held and adapted to be positioned so it has generally upper and lower surfaces, the housing including a circuit for converting an input voltage into a negative high voltage having sufficient value to ionize air, the circuit having high voltage and ground terminals, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing; a stand for the housing causing the housing upper surface to be positioned above the housing lower surface; a pad for the particulates adapted to be placed on a horizontal surface, the stand having a horizontal lower surface supported by the pad so that the stand sits on the pad and the housing is located above the pad and the collected particulates fall by gravity onto the pad.

2. The portable air ionizer of claim 1 wherein the plural electrodes include a sheet metal strip having an elongated base and plural triangles, the triangles extending substantially at right angles from the base; a dielectric board, the elongated base of the sheet metal strip being mounted on said board; each of the triangles having an apex remote from the base to provide a formation location for the negative ions.

3. The portable air ionizer of claim 1 wherein the housing includes a central region having an interior wall spaced from an exterior wall of the housing, the interior wall forming a well, a circuit being located in the well and being surrounded and held in place by potting compound filling the well and bonded to the interior wall.

4. The portable air ionizer of claim 3 wherein the ground plane and a connector between a source of the input voltage and the converting circuit are located between the interior and exterior walls.

5. The portable air ionizer of claim 1 wherein the pointed ends are arranged in two parallel rows each including three electrodes, the pointed ends of the two rows being aligned, the ground electrode having a planar surface and being proximate the lower surface, the two rows being spaced from each other by about ¾ inches, adjacent pointed ends of the same row being spaced from each other by about ½ inch, the pointed ends being in a plane disposed at an angle of about 70° relative to the planar surface of the ground electrode, the height of the points of the pointed ends being about ¼ inch above the ground electrode, the spacing of the points of the pointed ends being about 1/16 inch from an edge of the ground plane in the direction of the ground plane.

6. The portable air ionize of claim 1 further including a dielectric board on which said plural electrodes having pointed ends are mounted, a dielectric wall positioned between the ground plane electrode and the plural electrodes having pointed ends, said dielectric board being mounted so that an edge of said dielectric board abuts against the wall.

7. The portable air ionizer of claim 6 wherein said board is tilted upwardly with respect to said ground plane electrode, said pointed electrodes extending generally at right angles to said dielectric board.

8. The portable air ionizer of claim 7 wherein said electrodes are arranged in two parallel rows extending parallel to the wall, each of said rows including plural electrodes.

9. The portable air ionizer of claim 1 wherein the plural electrodes include a sheet metal strip having an elongated base and plural triangles, the triangles extending substantially at right angles from the base; a dielectric board, the elongated base of the sheet metal strip being mounted on said board; each of the triangles having an apex remote from the base to provide a formation location for the negative ions, the housing including a central region having an interior wall spaced from an exterior wall of the housing, the interior wall forming a well, a circuit being located in the well and being surrounded and held in place by potting compound filling the well and bonded to the interior wall, and further including a dielectric board on which said plural electrodes having pointed ends are mounted, a dielectric wall positioned between the ground plane electrode and the plural electrodes having pointed ends, said dielectric board being mounted so that an edge of said dielectric board abuts against the wall.

10. The portable air ionizer of claim 9 wherein the pointed ends are arranged in two parallel rows each including three electrodes, the pointed ends of the two rows being aligned, the ground electrode having a planar surface and being proximate the lower surface, the two rows being spaced from each other by about ¾ inches, adjacent pointed ends of the same row being spaced from each other by about ½ inch, the pointed ends being in a plane disposed at an angle of about 70° relative to the planar surface of the ground electrode, the height of the points of the pointed ends being about ¼ inch above the ground electrode, the spacing of the points of the pointed ends being about 1/16 inch from an edge of the ground plane in the direction of the ground plane.

11. The portable air ionizer of claim 10 wherein the input voltage is supplied by a jack connected to a coaxial cable, the housing including a connector for connecting voltage from the jack to the converting circuit and an opening for receiving the jack to enable the jack to be inserted into the connector.

12. The portable air ionizer of claim 9 wherein the input voltage is supplied by a jack connected to a cable, the housing including a connector for connecting voltage from the jack to the converting circuit and an opening for receiving the jack to enable the jack to be inserted into the connector.

13. The portable air ionizer of claim 1 wherein the pad is a dielectric material that can be cleaned of the collected particulates by a liquid solvent.

14. The portable air ionizer of claim 1 wherein the housing is fully supported by the stand so no portion of the housing contacts the pad.

15. The portable air ionizer of claim 14 wherein the stand is a dielectric.

16. The portable air ionizer of claim 15 wherein the electrodes are positioned and arranged and are energized by the negative high voltage so that smoke in a one cubic foot enclosure where the housing is located is precipitated so air in the housing appears to the eye to be clear of the smoke in less than one minute of operation of the ionizer, the smoke filling the enclosure so the enclosure appears to the eye to be opaque at the beginning of the one minute period.

17. The portable air ionizer of claim 16 wherein the electrodes are positioned and arranged and are energized by the negative high voltage so that the smoke above each of the openings proximate the electrodes having pointed ends swirls in a funnel-like pattern above each of the openings proximate the electrodes having pointed ends.

18. The portable air ionizer of claim 1 wherein the electrodes are positioned and arranged and are energized by the negative high voltage so that the air above each of the openings proximate the electrodes having pointed ends swirls in a funnel-like pattern above each of the openings proximate the electrodes having pointed ends.

19. A portable air ionizer comprising a dielectric housing small enough to be hand held and adapted to be positioned so it has generally upper and lower surfaces, the housing including: a circuit for converting an input voltage into a negative high voltage having sufficient value to ionize air, the circuit having high voltage and ground terminals, plural electrodes having pointed ends connected to be responsive to the negative high voltage at the high voltage terminal, the plural electrodes including a sheet metal strip having an elongated base and plural triangles, the triangles extending substantially at right angles from the elongated base of the strip; a dielectric board, the elongated base of the sheet metal strip being mounted on said board; each of the triangles having an apex remote from the base to provide a formation location for the negative ions, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing.

20. The portable air ionizer of claim 19 wherein the plural electrodes include a pair of said strips, each of said strips being mounted on said board, said board including a printed circuit connecting the strips to the high voltage terminal.

21. The portable air ionizer of claim 20 wherein said sheets are flat and extend along lines on the board that are substantially parallel to each other, the apices of the triangles being aligned with each other.

22. The portable air ionizer of claim 21 wherein each of the strips includes posts extending from the base in a direction opposite to the triangles, the dielectric board having apertures receiving the posts to mount the strip on the board, at least one of the posts being connected to the high voltage terminal.

23. The portable air ionizer of claim 19 wherein the strip includes posts extending from the base in a direction opposite to the triangles, the dielectric board having apertures receiving the posts to mount the strip on the board, at least one of the posts being connected to the high voltage terminal.

24. A portable personal air ionizer comprising a dielectric housing small and lightweight enough to be hand held and adapted to be positioned so it has generally upper and lower surfaces, the housing including: a central region having an interior wall spaced from an exterior wall of the housing, the interior wall forming a well, a circuit for converting an input voltage into a negative high voltage having sufficient value to ionize air, the circuit having high voltage and ground terminals, the circuit being located in the well and being surrounded and held in place by potting compound filling the well and bonded to the interior wall, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing.

25. The portable air ionizer of claim 24 wherein the ground plane and a connector between a source of the input voltage and the converting circuit are located between the interior and exterior walls.

26. A portable personal air ionizer comprising a dielectric housing small and lightweight enough to be hand held and adapted to be positioned so it has generally upper and lower surfaces, the housing including: a circuit for converting an input voltage into a negative high voltage having sufficient value to ionize air, the circuit having high voltage and ground terminals, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing, the pointed ends being arranged in two parallel rows each including three electrodes, the pointed ends of the two rows being aligned, the ground electrode having a planar surface proximate the lower surface, the two rows being spaced from each other by about $\frac{3}{4}$ inches, adjacent pointed ends of the same row being spaced from each other by about $\frac{1}{2}$ inch, the pointed ends being in a plane disposed at an angle of about 70° relative to the planar surface of the ground electrode, the height of the points of the pointed ends being about $\frac{1}{2}$ inch above the ground electrode, the spacing of the points of the pointed ends being about 1/16 inch from an edge of the ground plane in the direction of the ground plane.

27. A portable personal air ionizer comprising a dielectric housing small and lightweight enough to be hand held and adapted to be positioned so it has generally upper and lower surfaces, the housing including: a circuit for converting an input voltage into a negative high voltage having sufficient value to ionize air, the circuit having high voltage and ground terminals, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing; a dielectric board on which said plural electrodes are mounted having pointed ends, a dielectric wall positioned between the ground plane electrode and the plural electrodes having pointed ends, said dielectric board being mounted so that an edge of said dielectric board abuts against the wall.

28. The portable air ionizer of claim 27 wherein said board is tilted upwardly with respect to said ground plane electrode, said pointed electrodes extending generally at right angles to said dielectric board.

29. The portable air ionizer of claim 28 wherein said electrodes are arranged in two parallel rows extending parallel to the wall, each of said rows including plural electrodes.

30. A portable personal air ionizer comprising a dielectric housing small and lightweight enough to be hand held and adapted to be positioned so it has generally upper and lower surfaces, the housing including: a circuit for converting an input voltage into a negative high voltage having sufficient value to ionize air, the circuit having high voltage and ground terminals, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing, the input voltage being supplied by a jack connected to a coaxial cable, the housing including a connector for connecting voltage from the jack to the converting circuit and an opening for receiving the jack to enable the jack to be inserted into the connector.

31. A portable personal air ionizer comprising a dielectric housing small and lightweight enough to be hand held and adapted to be positioned so it has generally upper and lower surfaces, the housing including: a circuit for converting an input voltage into a negative high voltage having sufficient value to ionize air, the circuit having high voltage and ground terminals, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing; the electrodes being positioned and arranged and energized by the negative high voltage so that smoke in a one cubic foot enclosure where the housing is located is precipitated so air in the housing appears to the eye to be clear of the smoke in less than one minute of operation of the ionizer, the smoke filling the enclosure so the enclosure appears to the eye to be opaque at the beginning of the one minute period.

32. The portable air ionizer of claim 31 wherein the electrodes are positioned and arranged and are energized by the negative high voltage so that the smoke above each of the openings proximate the electrodes having pointed ends swirls in a funnel-like pattern above each of the openings proximate the electrodes having pointed ends.

33. A portable personal air ionizer comprising a dielectric housing small and lightweight enough to be hand held and adapted to be positioned so it has generally upper and lower surfaces, the housing including: a circuit for converting an input voltage into a negative high voltage having sufficient value to ionize air, the circuit having high voltage and ground terminals, plural electrodes having pointed ends connected to be responsive to the negative high voltage at the high voltage terminal, a ground plane electrode connected to the ground terminal, the housing further including an opening in proximity to each of the electrodes, the openings proximate the electrodes having pointed ends being on the upper surface, the opening proximate the ground plane electrode being on the lower surface, the openings and electrodes being positioned and arranged and the voltage applied to the plural electrodes being such that negative ions flow from the openings proximate the plural electrodes into the air, the negative ions causing particulates to fall by gravity, the negative ions flowing from the openings on the upper surface into the air without a fan being in or associated with the housing; the electrodes being positioned and arranged and energized by the negative high voltage so that air above each of the openings proximate the electrodes having pointed ends swirls in a funnel-like pattern above each of the openings proximate the electrodes having pointed ends.

* * * * *